U S008691954B2

US008691954B2

(12) United States Patent
Lee et al.

(10) Patent No.: US 8,691,954 B2
(45) Date of Patent: Apr. 8, 2014

(54) ANTIBODY TO PLACENTAL PROTEIN HAVING A REGULATING ACTION ON PROTEOLYTIC ACTIVITY

(76) Inventors: Jin-Pyo Lee, Tokyo (JP); Hoon Kim, Tokyo (JP)

(*) Notice: Subject to any disclaimer, the term of this patent is extended or adjusted under 35 U.S.C. 154(b) by 718 days.

(21) Appl. No.: 12/527,460

(22) PCT Filed: Feb. 15, 2008

(86) PCT No.: PCT/JP2008/052551
§ 371 (c)(1),
(2), (4) Date: Feb. 16, 2010

(87) PCT Pub. No.: WO2008/099928
PCT Pub. Date: Aug. 21, 2008

(65) Prior Publication Data
US 2010/0144027 A1   Jun. 10, 2010

(30) Foreign Application Priority Data
Feb. 16, 2007   (JP) ................................. 2007-036567

(51) Int. Cl.
*C07K 16/18* (2006.01)

(52) U.S. Cl.
USPC ..................................................... 530/387.9

(58) Field of Classification Search
None
See application file for complete search history.

(56) References Cited

U.S. PATENT DOCUMENTS

| 7,348,409 B2 * | 3/2008 | Garbe et al. .................. 530/350 |
| 2004/0224363 A1 | 11/2004 | Polyak et al. |
| 2005/0202508 A1 * | 9/2005 | Pasinetti ........................ 435/7.1 |

FOREIGN PATENT DOCUMENTS

| JP | 2004-344156 A | 12/2004 |
| JP | 2005-5115521 A | 4/2005 |
| JP | 2005-210901 A | 8/2005 |

OTHER PUBLICATIONS

Sagawa et al. Int. J. Legal Med. 117: 90-95 (2003).*
Minami et al. J. Dermatol. Sci. 36: 180-182, 2004.*
Baechle et al. J. Biol. Chem. 281(9): 5406-5415, 2006.*
J. L. Motoyama et al., "Identification of Dermcidin in Human Gestational Tissue and Characterization of its Proteolytic Activity," Biochemical and Biophysical Research Communications, Mar. 28, 2007, pp. 828-833, vol. 357.

\* cited by examiner

*Primary Examiner* — Christine J Saoud
(74) *Attorney, Agent, or Firm* — Westerman, Hattori, Daniels & Adrian, LLP

(57) ABSTRACT

The present invention is intended to provide a specific antibody to a protein that does not have a known protein motif structure but has proteolytic activity and regulating action on the activity of other proteases, cell invasiveness and smooth muscle contraction and relaxation, and is capable of treating, preventing and diagnosing various diseases. The protein is for the treatment, prevention or diagnosis of a disease selected from the group consisting of perinatal diseases, infertility, cancer, nervous system diseases, inflammatory diseases, immune diseases, cardiovascular diseases, endocrine diseases, viral infections, bacterial infections and prion diseases, and is shown in Sequence listing 1.

1 Claim, 5 Drawing Sheets

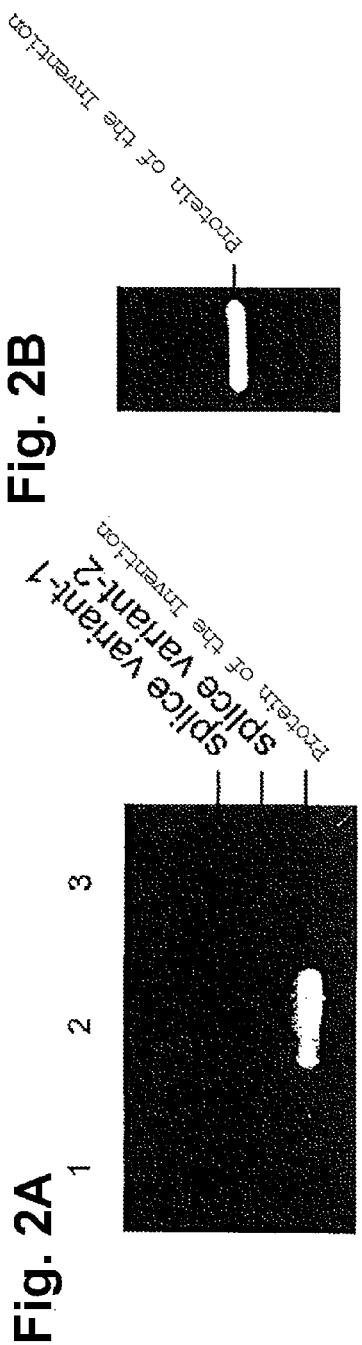
Fig. 2A
Fig. 2B
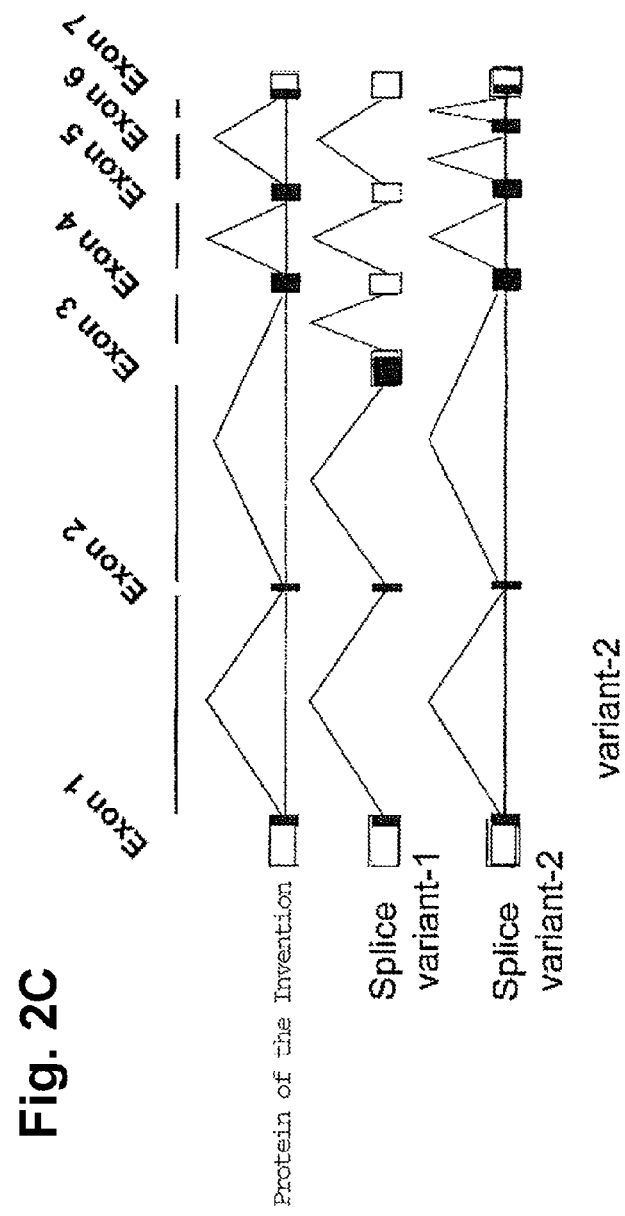
Fig. 2C

ANTIBODY TO PLACENTAL PROTEIN HAVING A REGULATING ACTION ON PROTEOLYTIC ACTIVITY

TECHNICAL FIELD

The present invention relates to a pharmaceutical composition for the treatment, prevention and diagnosis of a disease selected from the group consisting of perinatal diseases, cancer, nervous system diseases, inflammatory diseases, cardiovascular diseases, endocrine diseases, viral infections, bacterial infections and prion diseases. The pharmaceutical composition contains a protein with a regulating action on proteolytic activity or an antibody specific thereto.

BACKGROUND ART

Proteases that have been hitherto reported are classified into serine/threonine-, metallo-, cysteine- and aspartic-proteases and other classes of proteases comprising protein families characterized as having common protein motif structures. However, proteases that do not possess these structures but have regulating action on the activity of other proteases, cell invasiveness, and smooth muscle contraction and relaxation, as well as proteolytic activity, have not yet been reported.

The inventors of the present invention extracted, purified and isolated an oxytocin receptor active substance from human placental tissue, determined the partial amino acid sequence of the substance (Patent Documents 1 and 2, and Non-Patent Document 1), further determined the structure of the gene encoding the protein (Patent Document 3 and Non-Patent Document 1), and showed the presence of splice variants of the gene in the term human placenta (Non-Patent Document 1). The inventors investigated the physiological action of the subject protein and disclosed that the protein has relaxing activity on uterine smooth muscles (Patent Document 3) and proteolytic activity (Patent Document 4 and Non-Patent Document 1). However, it was not shown whether the subject protein has regulating action on the activity of other proteases, that is, its usefulness in the treatment, prevention and diagnosis of various diseases; regulating activity on cell invasiveness, that is, its usefulness in the treatment of cancer and related diseases; contracting and relaxing activities on uterine smooth muscles or in broad terms, regulating activity on the function of uterine smooth muscles, that is, its usefulness in the treatment, prevention and diagnosis of various perinatal diseases.

Patent Document 1: JP-A No. 2000-095797
 Patent Document 2: JP-A No. 2003-226699
 Patent Document 3: JP-A No. 2005-210901
 Patent Document 4: JP-A No. 2004-344156
 Non-Patent Document 1: J. P. Lee Motoyama (Shizuo Motoyama), H. Kim-Motoyama (Kaoru Motoyama), P. Kim, H. Nakagama, K. Miyagawa, K. Suzuki, Identification of dermcidin in human gestational tissue and characterization of its proteolytic activity, Biochem. Biophys. Res. Commun. 357 (2007), pp. 828-833

DISCLOSURE OF THE INVENTION

Problems to be Solved by the Invention

The present invention provides a novel pharmaceutical composition containing a protein with no known protein motif structure but with regulating action on the activity of other proteases, cell invasiveness and smooth muscle contraction and relaxation, as well as proteolytic activity. This pharmaceutical composition therefore presents great potential for the treatment, prevention and diagnosis of various diseases.

Means for Solving the Problems

The inventors of the present invention found remarkable characteristics of the protein, that is, it does not have a known protein motif structure but has regulating action on the activity of other proteases, cell invasiveness, and smooth muscle contraction and relaxation. The inventors thereby completed the identification of the novel pharmaceutical composition of a protein for the treatment, prevention and diagnosis of various diseases.

The present invention provides a regulator of proteolytic activity, cell invasiveness or smooth muscle contraction and relaxation, and this regulator contains a protein shown in SEQ ID NO:1 or an antibody specific thereto.

The present invention also provides a recombinant vector for the regulation of proteolytic activity, cell invasiveness or smooth muscle contraction and relaxation. The recombinant vector contains a gene shown in SEQ ID NO:2, which encodes the protein shown in SEQ ID NO:1, or a gene shown in SEQ ID NO:3 or SEQ ID NO:4, which is a splice variant thereof.

The present invention also provides a pharmaceutical composition for the treatment, prevention or diagnosis of a disease selected from the group consisting of perinatal diseases, infertility, cancer, nervous system diseases, inflammatory diseases, immune diseases, cardiovascular diseases, endocrine diseases, viral infections, bacterial infections and prion diseases. The pharmaceutical composition contains the protein shown in SEQ ID NO:1 or an antibody specific thereto.

The present invention also provides a recombinant vector for the treatment, prevention or diagnosis of a disease selected from the group consisting of perinatal diseases, infertility, cancer, nervous system diseases, inflammatory diseases, immune diseases, cardiovascular diseases, endocrine diseases, viral infections, bacterial infections and prion diseases. The recombinant vector contains the gene shown in SEQ ID NO:2, which encodes the protein shown in SEQ ID NO:1, or the gene shown in SEQ ID NO:3 or SEQ ID NO:4, which is a splice variant thereof.

Effects of the Invention

Based on the regulating action on the activity of other proteases, cell invasiveness, and smooth muscle contraction and relaxation, as well as the proteolytic activity of the protein of the present invention, it is possible to develop a pharmaceutical composition comprising the protein for the treatment, prevention and diagnosis of various diseases, including perinatal diseases (e.g., recurrent pregnancy loss, infertility, abortion, preterm delivery (premature delivery), intrauterine fetal growth retardation, intrauterine fetal death and preeclampsia/eclampsia); infertility; carcinogenesis and cancer invasion/metastasis; nervous system diseases; inflammatory diseases; immune diseases; cardiovascular diseases (e.g., atherosclerosis); endocrine diseases (e.g., diabetes mellitus); and infectious diseases (e.g., viral and bacterial infections, and prion diseases).

BRIEF DESCRIPTION OF THE DRAWINGS

FIG. 2 shows the gene expression of the protein of the present invention, and two splice variants thereof in the human placenta. FIG. 2A shows the results obtained by reverse transcription polymerase chain reaction (RT-PCR) amplification of the mRNAs of the protein of the present invention and splice variants thereof from term human placental tissues. Lanes 1 and 2 represent the RT-PCR products of the mRNA from the villus parenchyma of different placentas, and lane 3 indicates the RT-PCR product of the mRNA from the amniotic membrane. FIG. 2B shows the gene expression of the protein of the present invention in the first trimester human placenta. FIG. 2C presents a schematic representation of these genes.

FIG. 5 presents the effect of various agents on myometrial contraction in a Magnus apparatus using myometrial preparations from a term pregnant rat uterus.

BEST MODE FOR CARRYING OUT THE INVENTION

Figure 1B:
FIG. 1B shows hematoxylin-eosin staining.
Figure 1D:
FIG. 1D presents negative control staining The original magnification is 50× for (A, B) and 400× for (C, D).
Figure 1A:
FIG. 1A shows the immunostaining of the chorionic villi of a first trimester human placenta using a specific antibody against the protein of the present invention.
Figure 1C:
FIG. 1C demonstrates a higher magnification view of FIG. 1.

The protein of the present invention contained in the regulator of proteolytic activity, cell invasiveness, or smooth muscle contraction and relaxation, as well as in the pharmaceutical composition for the treatment, prevention or diagnosis of diseases disclosed herein may be derived from the placenta, amnion, decidua, or maternal factors circulating in the placenta, for example, maternal blood cell components such as leukocytes, particularly maternal monocytes or lymphocytes. However, the protein derived from any type of human tissues during gestation is within the scope of this invention. Also within the scope of this invention is the protein derived from any type of non-gestational human tissues whether it be brain, nervous, tumor, inflammatory or related tissues, or under any conditions whether it be physiological or pathological conditions. Furthermore, the protein derived from any species other than humans is included within the scope of this invention.

As used herein, the term "an antibody specific to a protein shown in SEQ ID NO:1" means an antibody that specifically reacts with the protein shown in SEQ ID NO:1. Whether the prepared antibody specifically reacts with the protein shown in SEQ ID NO:1 can be easily confirmed by conducting assays known in the art, such as Western blotting or enzyme-linked immunosorbent assay.

The recombinant vector of the present invention can be easily prepared by cloning a gene shown in SEQ ID NO:2, which encodes the protein shown in SEQ ID NO:1, or a gene shown in SEQ ID NO:3 or SEQ ID NO:4, which is a splice variant thereof, into a suitable vector using methods known in the art, such as TA-cloning or restriction enzyme mediated cloning methods.

The protease whose activity is regulated by the protein of the present invention may be any proteases. As used herein, the term "regulation of proteolytic activity" means enhancement or attenuation of proteolytic activity. The term "regulation of cell invasiveness", as used herein, means enhancement or attenuation of cell invasiveness. The term "regulation of smooth muscle contraction and relaxation", as used herein, means induction of smooth muscle contraction or relaxation. The smooth muscles may be from any organ, but preferably uterine smooth muscles.

As used herein, the term "treatment" means the partial or complete cure for a disease or condition. The term "prevention", as used herein, means the prevention of not only the onset but also the spread of a disease or condition. The term "diagnosis", as used herein, means the evaluation of a disease or condition.

It is conceived that proteases are extensively involved in various physiological functions including tissue remodeling, activation of a latent protein precursor, embryogenesis and the mechanism of placental implantation. Proteases are also shown to be strongly involved in mechanisms underlying carcinogenesis and cancer invasion/metastasis, as well as the pathophysiology of various diseases, such as inflammatory diseases including arthritis and periodontitis; perinatal diseases such as preeclampsia, abortion and preterm delivery; and infertility.

Proteases not only degrade proteins but also participate in the regulation of a wide range of organismal functions by processing bioactive proteins through proteolysis. For example, in the blood coagulation cascade, precursor proteins are activated by proteolysis. Moreover, proteolysis is suggested to be involved in the control of important cellular functions such as DNA replication, cell cycle progression, proliferation, apoptosis, differentiation/dedifferentiation, migration and invasion.

In the extracellular microenvironment, most of the proteases are localized on the cell surface and in the immediate pericellular space. Proteases that are secreted extracellularly regulate the functions of bioactive proteins such as growth factors, hormones, cytokines, receptor proteins or integrins in the pericellular space by processing these proteins through proteolysis. Proteases have been found to regulate the functions of bioactive cell surface or membrane proteins by forming an intricate network on the cell surface, and further control various cellular functions in response to changes in the extracellular environment by transmitting signals intracellularly.

Proteolysis regulates a wide variety of cellular functions including cell invasiveness. With regard to the invasion of cancer and trophoblast cells, cells can establish invasion into the surrounding tissues not only by degrading extracellular matrix proteins successively at the leading edge of invading cells, but also by controlling various cellular behaviors such as cell proliferation, evasion of attacks from immune cells, escape from apoptosis, migration and angiogenesis through pericellular proteolysis.

Cell invasiveness underlies various physiological processes such as neuronal plasticity, mechanisms of wound healing, inflammation, immune response and angiogenesis as well as cancer-cell invasion/metastasis. While cell invasiveness is involved in the pathophysiology of a wide variety of diseases, trophoblast cell invasiveness is essential for mechanisms of pregnancy maintenance. In normal placentation, trophoblast cells invade the uterine decidua/myometrium and then proceed to invade the endothelium of maternal arterioles to establish blood flow to the placenta. As described above, the molecular mechanisms of cancer and trophoblastic cell invasion share many common properties. However, while cancer cells are characterized by their uncontrolled invasion, the invasion of trophoblasts is characterized by being confined temporally to early pregnancy, and spatially to the first third of the maternal myometrium. Such invasion must be stringently controlled during human pregnancy since reduced trophoblastic invasion causes various diseases such as intrauterine fetal growth retardation and preeclampsia/eclampsia, as well as infertility, recurrent pregnancy loss, abortion and preterm delivery and intrauterine fetal death. On the other hand, increased trophoblastic invasion causes choriocarcinoma with a highly accelerated metastatic potential. It is widely recognized that trophoblast cell invasiveness is closely involved in the molecular mechanisms of pregnancy maintenance and parturition. At the same time, trophoblast cell invasiveness is suggested to be closely associated with the pathophysiology of perinatal diseases (e.g., recurrent pregnancy loss, abortion, preterm delivery, intrauterine fetal growth retardation/fetal death and preeclampsia/eclampsia) and infertility, or the mechanisms underlying carcinogenesis and metastasis of choriocarcinoma.

In addition to cell invasiveness, another cellular function that is regulated by proteolysis is molecular regulation of smooth muscle contraction and relaxation. For successful pregnancy maintenance and parturition, exquisite regulation of myometrial contraction and relaxation is necessary, together with the stringent control of trophoblast cell invasiveness. Uterine growth commences after fertilization and implantation to accommodate the growing embryo/fetus. However, during pregnancy, myometrial contraction, which could eventually result in the expulsion of the conceptus, must be suppressed so that the uterine smooth muscles remain quiescent while maintaining a basal uterine tone. On the other hand, excessive uterine contractions cause abortion or preterm delivery as well as reduction in placental blood flow, a possible cause of hypoxic fetal brain injury, cerebral palsy, fetal asphyxia, intrauterine fetal death or other related conditions. From the beginning of labor, uterine smooth muscles start regular contractions, which must be sufficiently strong in order to expel the conceptus from the uterus until the completion of parturition. On the other hand, excessive uterine contractions during labor are accompanied by an increased risk of fetal hypoxia and brain injury leading to fetal asphyxia and intrauterine fetal death due to a reduction in placental blood flow. Therefore, uterine contractions during labor must be stringently regulated. Meanwhile, suppression of myometrial contractions during parturition might result in prolonged labor, which is also a probable cause of fetal asphyxia or intrauterine fetal death. Furthermore, suppression of myometrial contractions could result in post-term pregnancy, which might also cause fetal asphyxia or intrauterine fetal death as a result of uteroplacental insufficiency. As described above, exquisite control of myometrial contraction and relaxation is crucial for pregnancy maintenance and parturition, and any abnormalities thereof may contribute to the pathogenesis of perinatal diseases (e.g., abortion, preterm delivery, fetal asphyxia, intrauterine fetal death, cerebral palsy and recurrent pregnancy loss) or infertility.

The molecular mechanisms of myometrial contraction and relaxation remain largely unknown. As an illustration, the physiologic role of oxytocin in myometrial contraction may be taken as an example. Oxytocin, the structure of which was determined in the 1950s, is a potent uterotonic posterior pituitary hormone widely used clinically to induce and augment human labor. The expression of myometrial oxytocin receptors has been reported to rapidly increase in late gestation around the onset of labor, implicating oxytocin in the mechanisms of initiation of labor and myometrial contractions during parturition. On the other hand, it has been reported that mice lacking the gene encoding oxytocin developed normally and were able to deliver normal fetuses at term. In these knock-out mice, parturition was unaffected. There remains much to be learned regarding the relationships between oxytocin and the mechanisms of initiation of labor and myometrial contractions during parturition. On the other hand, the molecular mechanisms of myometrial quiescence during pregnancy have not yet been fully elucidated. Thus, the prediction, prevention and treatment of preterm delivery, a major consequence of the premature disruption in myometrial quiescence, constitute one of the most serious problems in perinatal medicine.

It is widely recognized that, other than paracrine or endocrine oxytocin-oxytocin receptor interactions, the molecular mechanisms of myometrial contraction and relaxation involve modification of receptor proteins or ligands thereof by proteolysis at or near the myometrial cell surface.

As such, proteolysis regulates the functions of various bioactive proteins by proteolytic processing and thereby participate in the regulation of a wide range of physiological functions, including previously mentioned cell invasiveness and smooth muscle contraction and relaxation, as well as cell proliferation, apoptosis, angiogenesis, migration, immune response, inflammatory reaction, wound healing, neuronal plasticity, and other related functions.

Therefore, proteolysis is extensively involved in the pathogenesis of various diseases. It is closely related to the mechanisms underlying carcinogenesis and cancer cell metastasis as well as cancer cell invasion as described above. In addition, proteolysis is also closely involved in the pathophysiology of inflammatory diseases, immune diseases, nervous system diseases, cardiovascular diseases (e.g., atherosclerosis), endocrine diseases (e.g., diabetes mellitus) and infectious diseases (e.g., viral infection and bacterial infections, and prion diseases).

Furthermore, proteolysis is also closely associated with the mechanisms of pregnancy-associated diseases, as previously mentioned. Examples of conditions brought about by the association between proteolysis and pregnancy-associated diseases include perinatal diseases (e.g., recurrent pregnancy loss, abortion and premature delivery, intrauterine fetal growth retardation and fetal death, and preeclampsia/eclampsia), infertility and choriocarcinoma. Their pathogenensis is associated with the disruption of the aforementioned mechanisms regulating trophoblast cell inavasiveness. Other conditions include perinatal diseases (e.g., abortion, premature delivery, fetal asphyxia, intrauterine fetal death and cerebral palsy), infertility and recurrent pregnancy loss, their pathogenesis being associated with myometrial contracting or relaxing activities and involving the disruption of proteolysis-regulated mechanisms thereof.

In addition, there have been many reports documenting the close relationship between proteolysis and the pathogenesis of pregnancy-associated diseases, particularly preeclampsia/eclampsia, a serious complication of human pregnancy. This complication can result in the maternal and fetal mortality, and several reports have implicated proteolysis in the pathogenesis of preeclampsia/eclampsia. Reduced trophoblast invasion is one of the mechanisms involved in the pathogenesis of preeclampsia/eclampsia, while proteolysis is closely associated with trophoblast cell invasion, as described above. As an additional example implicating the relationship between proteolysis and the pathogenesis of preeclampsia, it has also been reported that the proteolytic activity in the microvilli at the surface layer of syncytiotrophoblasts is extensively involved in the pathophysiology of preeclampsia/eclampsia. Syncytiotrophoblasts are present at the interface between the maternal circulation and the fetus/placenta, and the microvillus membrane is partly shed to the maternal circulation. Unidentified proteolytic activities in the microvillus membrane are reported to be involved in the pathogenesis of the maternal symptoms of preeclampsia, such as hypertension, proteinuria and edema. The presence of a vascular endothelial growth factor (VEGF) receptor on the trophoblastic cell membrane is another example suggesting the relationship between proteolysis and preeclampsia/eclampsia. The extracellular domain of the VEGF receptor (sFln1), which is shed by proteolysis at the trophoblastic cell surface and released into the maternal circulation, is reported to be implicated in the pathogenesis of preeclampsia/eclampsia. Details of the proteases responsible for the shedding of sFln1 have not yet been fully characterized.

As described above, it is becoming evident that proteolysis is involved in the pathophysiology of a wide variety of diseases, and it is possible to develop a therapeutic, prophylactic or diagnostic drug which is specific to a particular disease using a substance that regulates the proteolytic activity involved in the pathogenesis of the disease. Also, even for a disease in which certain proteolytic activity is not directly involved in its pathophysiology, if the functions of proteins that are directly involved in the pathogenesis of the disease are regulated by a particular proteolytic activity, it is possible to develop a therapeutic, prophylactic or diagnostic drug which is specific to that disease on the basis of a substance that regulates the proteolytic activity.

However, although it has already been revealed that proteases not only degrade proteins but also are closely involved in the regulation of a wide range Of physiological functions as well as the pathogenesis of various diseases by controlling the functions of various bioactive proteins by proteolytic processing, the underlying molecular mechanisms thereof have not been fully elucidated to date. For example, mechanisms of the activation of pro-matrix metalloproteinases by proteolysis on the cell surface and in the immediate pericellular space, and precise mechanisms linking matrix metalloproteinases and cellular functions including cell invasiveness remain to be clarified. Moreover, mechanisms of the proteolytic activation of precursor proteins in the blood coagulation cascade have not yet been fully clarified. At the same time, among the extremely wide range of physiological functions and pathophysiologies of various diseases of which their molecular mechanisms are related to proteolytic activity, there are many instances in which the relevant proteolytic activity could not be attributed to any already-known proteases.

Therefore, a pharmaceutical composition of the present invention containing the protein shown in SEQ ID NO:1 with no known protein motif structure but has remarkable characteristics of having regulating action on the activity of other proteases, cell invasiveness and smooth muscle contraction and relaxation, or an antibody specific thereto can be used in the treatment, prevention or diagnosis of perinatal diseases, infertility, cancer, nervous system diseases, inflammatory diseases (e.g., colitis, arthritis and wound healing), immune diseases, cardiovascular diseases (e.g., atherosclerosis), endocrine diseases (e.g., diabetes mellitus), viral infections (e.g., HIV and Kaposi's sarcoma), bacterial infections or prion diseases. Preferably, the perinatal diseases mentioned above include recurrent pregnancy loss, abortion, preterm delivery, intrauterine fetal growth retardation, intrauterine fetal death and preeclampsia/eclampsia. The above-mentioned cancer may be any type of cancer, tumor or sarcoma: tumor may either be a solid tumor or a non-solid tumor.

The pharmaceutical composition of the present invention containing the protein shown in SEQ ID NO:1 or an antibody specific thereto is preferably used in the treatment, prevention or diagnosis of a disease selected from the group consisting of recurrent pregnancy loss, abortion, preterm delivery, intrauterine fetal growth retardation, intrauterine fetal death, preeclampsia/eclampsia, infertility, cancer, viral infections and bacterial infections.

The vector containing the gene shown in SEQ ID NO:2, which encodes the protein shown in SEQ ID NO: 1, or the gene shown in SEQ ID NO:3 or SEQ ID NO:4, which is a splice variant thereof, can be used in the treatment, prevention or diagnosis of a disease selected from the group consisting of perinatal diseases, infertility, cancer, nervous system diseases, inflammatory diseases, immune diseases, endocrine diseases, viral infections, bacterial infections and prion diseases. Preferably, the vector is used in the treatment, prevention or diagnosis of a disease selected from the group consisting of recurrent pregnancy loss, abortion, preterm delivery, intrauterine fetal growth retardation, intrauterine fetal death, preeclampsia/eclampsia, infertility, cancer, viral infections and bacterial infections.

A person ordinarily skilled in the art would understand that there are many ways to achieve expression of the subject gene in a target tissue, and any suitable method may be employed. For example, the subject gene may be incorporated into a viral vector such as, but not limited to, adenovirus, adeno-associated virus, retrovirus, or vaccinia or other pox virus (e.g., avipoxvirus). Techniques for inserting a gene into such vectors are well known in the art. A retroviral vector may additionally incorporate a gene for a selectable marker and/or a target moiety, such as a gene that encodes a ligand for a receptor on a specific target cell, to render the vector target specific. Targeting may also be accomplished using an antibody by methods known in the art. A vector containing the subject gene can be used in the treatment, prevention or diagnosis of the above-mentioned diseases by either administering the vector into the target tissue by injection, inhalation, topical application or other methods known in the art, or isolating cells such as blood cells from the patient, introducing the vector into the cells and then placing the modified cells back into the patient. Examples of suitable vector include viral vectors. If the vector is used for diagnostic purposes, one part of the sequence of the gene shown in SEQ ID NO:2, or of the gene shown in SEQ ID NO:3 or SEQ ID NO:4, which is a splice variant thereof, may be detectably labeled. Appropriate labels include, without limitation, radioisotopes.

The pharmaceutical composition, recombinant vector and regulator of the present invention may be used on their own or combined with other active substances according to the present invention. These components may optionally also be used with other pharmacologically active substances.

Suitable preparations of the pharmaceutical composition include for example solutions, particularly solutions for injection (i.e., subcutaneous (s.c.), intravenous (i.v.) and intramuscular (i.m.) administration) and infusion, or emulsions. Solutions are prepared in the usual way, e.g. with the addition of isotonic agents, preservatives such as p-hydroxybenzoate, or stabilizers such as alkali metal salts of EDTA, optionally using emulsifiers and/or dispersants, while if water is used as the diluent, for example, organic solvents may optionally be used as solvating agents or dissolving aids, and transferred into injection vials, ampoules or infusion bottles.

The preparations are administered by the usual method, preferably by s.c., i.v., or i.m. route. The dosages are appropriately selected depending on the body weight, the route of administration, individual response to the active substance, and the time or interval over which the active substance is administered. The amount of the protein of the present invention in the preparations is generally in the range of about 100 μg to 50 mg/kg bodyweight of the patient. Suitable administration volumes depend on many factors including the patient's size and are typically in the range of about 0.1 mL to 10 mL.

EXAMPLE 1

(Purification and Identification of the Protein of the Present Invention)

The protein of the present invention is derived from the same precursor protein as a novel oxytocin receptor active substance identified in the human placenta by the inventors of the present invention (JP-A No. 2000-095797). Determination of the amino acid sequence of the protein of the present invention isolated and purified from term human placental tissue was achieved using the same technique described in Examples 1 to 7 of JP-A No. 2003-226699 and Non-Patent Document 1. In brief; human placenta (approximately 500 g wet weight) obtained after full term uncomplicated vaginal delivery was immediately frozen in liquid nitrogen, pulverized and then extracted with four volumes of water (95° C.) for 10 minutes. Thereafter, acetic acid at a final concentration of 1 N was added and the mixture was homogenized using a Polytron homogenizer. Subsequently, acetone at a final concentration of 80% was added and the resulting mixture was centrifuged. The supernatant was concentrated to obtain a crude extract. After purification of the crude extract by preparative reverse phase high-performance liquid chromatography (HPLC) and cation exchange HPLC using radioreceptor assay for oxytocin in order to monitor the activities of each HPLC fraction, a single active fraction corresponding to the peak of absorbance at 280 nm was obtained. The active fraction was further separated by reverse phase HPLC to obtain four active fractions. From the most hydrophobic fraction, partial amino acid sequences of the protein of the present invention shown in SEQ ID NO:5 and SEQ ID NO:6 were obtained by conventional amino acid sequencing analysis. In each cycle of the protein sequencing analysis of the aforementioned active fraction, equimolar amounts of two amino acid residues each from two peptide sequences shown in SEQ ID NO:5 and SEQ ID NO:6, were recovered. The radioreceptor assay for oxytocin was performed following the method described in Example 1 of JP-A No. 2000-095797. That is, the in vitro radioreceptor assay was conducted according to a conventional method using a crude membrane fraction prepared from human term pregnant myometrial tissue. As the labeled ligand, $^{125}$I-ornithine vasotocin analogue was used, which has a high specificity and selectivity for the oxytocin receptor as well as a high specific radioactivity. This radioreceptor assay was used to monitor each purification step. Subsequently, the protein of the present invention having an amino acid sequence shown in SEQ ID NO:1 was identified. Immunohistochemical staining was carried out using an antibody produced by the inventors of the present invention that is specific to the protein of the present invention. The specific rabbit polyclonal antibody was generated against the chemically synthesized N-terminal eight amino acid sequence of the peptide shown in SEQ ID NO:6, which is one of the partial amino acid sequences disclosed in the present invention. For control staining, a rabbit polyclonal antibody was generated against the chemically synthesized eight amino acid sequence (GSGNQKGL) not contained in any protein databases. Each of the antigen peptides was conjugated to bovine thyroglobulin carrier protein, and rabbits were immunized with the conjugate according to a conventional method. The IgG fraction of the rabbit antisera was affinity purified using the corresponding antigen peptide to obtain a high titer antibody specific to the protein of the present invention at a final concentration of 0.108 mg/mL (0.448 mg/mL for the control antibody). Immunohistochemical analysis demonstrated that the protein of the present invention was localized at the surface layer of syncytiotrophoblasts of the first trimester human placenta (FIG. 1). The syncytiotrophoblast cell layer is located at the maternal-fetal interface and participates in the maintenance of maternal-fetal homeostasis through the exchange of gases and nutrients between mother and fetus, or the production of hormones, growth factors, cytokines, proteases and other bioactive substances. Thus, these morphological findings corroborate our statements that the protein of the present invention might be closely involved in the mechanisms of pregnancy maintenance and parturition.

In addition, it became clear that in each step of the isolation and purification of the protein of the present invention, its biochemical properties were closely associated with those of the antimicrobial peptides human neutrophil defensin 1 and human neutrophil defensin 2. That is, during the purification steps of the protein of the present invention shown in Examples 1 to 7 of JP-A No. 2003-226699 and Non-Patent Document 1, N-terminal amino acid sequencing and matrix-assisted laser desorption/ionization-time of flight (MALDI-TOF) mass spectrometric analysis revealed that most of the constituents of the active fraction in the cation exchange HPLC, which was followed by the final reverse phase HPLC, were human neutrophil defensin 1 and human neutrophil defensin 2. At the same time, it has also become evident that among the four active fractions in the final reverse phase HPLC, human neutrophil defensin 1 and human neutrophil defensin 2 were obtained from the three fractions except the fraction from which the protein of the present invention was obtained. These results indicate the association of the biochemical properties of the protein of the present invention with those of the antimicrobial peptides human neutrophil defensin 1 and human neutrophil defensin 2. These chromatographic profiles strongly imply the association of the physiologic activity of the protein of the present invention and its antibacterial, antimicrobial, antiviral and anti-prion activities.

EXAMPLE 2

(Cloning of the Gene Encoding the Protein of the Present Invention and the Splice Variants Thereof)

Cloning of the gene of the protein of the present invention from term human placental tissue was performed following the same method described in the Examples of JP-A No. 2005-210901 and Non-Patent Document 1, whereas cloning of the two splice variants was conducted using the same method described in Non-Patent Document 1. The gene shown in SEQ ID NO:2 was identified as the gene encoding the protein of the present invention, and those in SEQ ID NO:3 and SEQ ID NO:4 were identified as the two splice variants. Cloning of the gene of the protein of the present invention from the first trimester human placenta was performed according to the methods described above. In brief, a Blast search specified a 21 nucleotide sequence on chromosome 21 encoding the C-terminal 7 amino acid sequence of a 29 amino acid peptide shown in SEQ ID NO:6, which was a partial amino acid sequence of the protein of the present invention obtained from the human placenta. Subsequently, genes were predicted computationally within the 7000 base pair (bp) region around the specified 21 by sequence on human chromosome 21 using various gene prediction programs. Among the several gene structures predicted in silica, FGENES predicted a gene composed of five exons encoding the amino acid sequences shown in SEQ ID NO:5 and SEQ ID NO:6, which are partial amino acid sequences of the protein of the present invention obtained from the human placenta. Other gene predicting programs failed to predict relevant genes. Lastly, it was confirmed by RT-PCR that the predicted gene was expressed in the term human placenta, and the cloning of the gene of the protein of the present invention was completed following determination of the nucleotide acid sequences of the 5'- and 3'-untranslated regions by RT-PCR.

Furthermore, the expression of two splice variants of the gene encoding the protein of the present invention in the term human placenta and amniotic membrane was confirmed by RT-PCR. Two novel exons not contained in any gene databases and not predicted by any gene prediction programs, each from the two splice variants were specified in the intron regions of the gene of the protein of the present invention composed of five exons. That is, a novel gene structure composed of seven exons was identified in the subject region on human chromosome 21.

To date, there have been no reports demonstrating the expression of the two splice variants of the present invention in any organs or tissues other than the human placenta. RT-PCR also failed to demonstrate the expression of these splice variants in the first trimester human placenta (FIG. 2B). (Therefore, these two splice variants were shown to be expressed in a spatiotemporally restricted manner starting from the establishment of pregnancy. Thus, the expression of these three related genes is speculated to be regulated exquisitely throughout the entire course of pregnancy.

EXAMPLE 3

(Control of the Activity of Other Proteases by the Protein of the Present Invention)

Figure 3A:
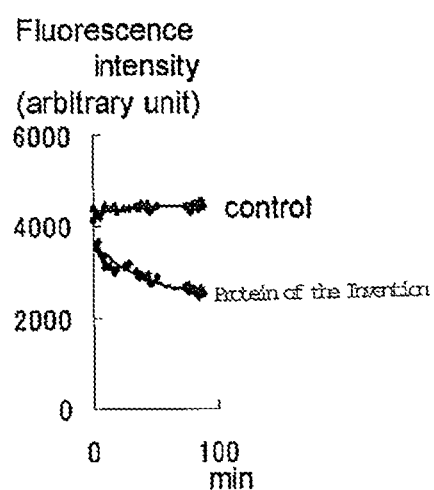
FIG. 3A shows the amidolytic activity of the protein of the present invention, which was obtained by immunoprecipitation from JAR cells, against the fluorescent peptide substrate for trypsin.
Figure 3C:
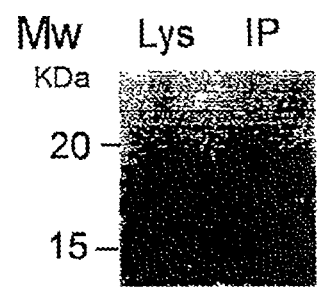
FIG. 3C shows the Western blot of a crude lysate of JAR cells (lane 1) and the immunoprecipitated protein of the present invention from JAR cells (lane 2) using a specific antibody against the protein of the present invention. Lane 1 is a gelatin zymogram showing the activation by the protein of the present invention obtained by immunoprecipitation from JAR cells in the presence of ethylene diamine tetra-acetic acid (EDTA) (lane 1) and a control reaction without adding the protein of the present invention (lane 2).
Figure 3B:
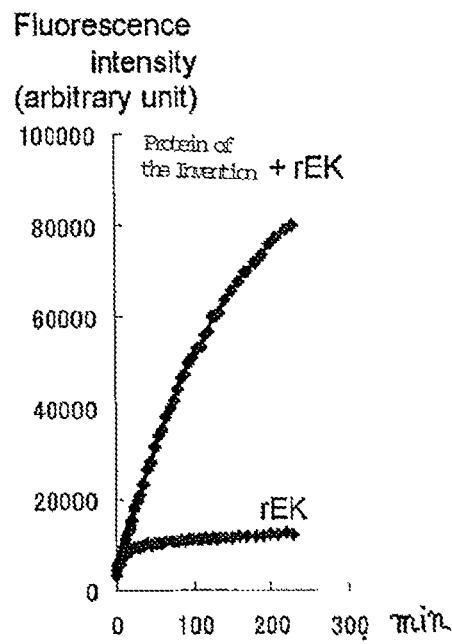
FIG. 3B presents the amidolytic activities of enterokinase and/or the protein of the present invention against the fluorescent peptide substrate.

Proteolytic activity of the protein obtained by immunoprecipitation using the specific antibody of the present invention from JAR cells was determined by adding the protein to a fluorescent peptide substrate for trypsin, and measuring the amount of increase in fluorescence intensity resulting from substrate cleavage. The addition of the protein of the present invention to the substrate alone resulted in a slight quenching of fluorescence instead of an increase in fluorescence intensity resulting from substrate cleavage (FIG. 3A). Fluorescence quenching was considered to result from the binding of the protein of the present invention to the fluorescent peptide substrate and the subsequent conformational change of the fluorescent peptide substrate. However, when the protein of the present invention was added to the fluorescent peptide substrate together with enterokinase, a significant rapid increase in fluorescence intensity was observed (FIG. 3B). The addition of enterokinase alone to the substrate did not elicit a rapid increase in fluorescence intensity resulting from substrate cleavage, demonstrating a considerably low level of proteolytic activity (FIG. 3B). That is, it was found that a minimal proteolytic activity exhibited by enterokinase alone was significantly enhanced by the protein of the present invention immunoprecipitated from JAR cells.

Figure 3D:
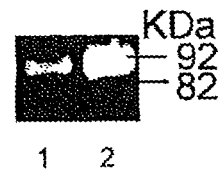

From the results described above, it was clearly shown that the protein of the present invention has a physiologic activity of enhancing the proteolytic activity of enterokinase, which is a distinct protease from the protein of the present invention. Moreover, the protein of the present invention indirectly acts on a substrate against which it does not directly exhibit proteolytic activity, by modifying the activity of other protease. Subsequently, Western blotting of a crude lysate of JAR cells (lane 1) and the immunoprecipitated protein of the present invention from JAR cells (lane 2) was performed using the specific antibody described above. Western blotting demonstrated that the protein of the present invention migrated as a single band at about 19 kDa (FIG. 3C), indicating the specific binding of our antibody described above to the protein of the present invention. FIG. 3D shows that the protein of the present invention, using the immunoprecipitated protein from human JAR cells, possesses proteolytic activity, which has also been documented by the inventers of the present invention using the recombinant protein of the present invention obtained from *E. coli* (Patent Document 6 and Non-Patent Document 1), in addition to the regulating action on the activity of other proteases. Gelatin zymography demonstrated that pro-matrix metalloproteinase-9 was activated by the immunoprecipitated protein of the present invention to generate active 82 KDa matrix metalloprotease-9 (FIG. 3D, lane 1) when incubated overnight at 25° C. with the addition to the reaction of phenanthroline, a matrix metalloproteinase inhibitor. These results indicate that the activation of pro-matrix metalloproteinase-9 did not involve autocatalytic mechanism by metalloproteinase-9 but depended solely on the proteolytic activity of the protein of the present invention. This finding confirms the proteolytic activity of the immunoprecipitated protein of the present invention from human JAR cells.

EXAMPLE 4

(Regulation of Cell Invasiveness by the Protein of the Present Invention)

The preparation of recombinant protein of the present invention in *E. coli* was carried out according to the method described in the Examples of JP-A No. 2005-210901 and Non-Patent Document 1. In brief, the preparation of an expression vector and the recombinant protein was carried out using the Affinity LIC Cloning and Protein Expression Kit (Stratagene, Inc.). A portion of the nucleotide acid sequence encoding the protein shown in SEQ ID NO:1 was inserted into the LIC cloning vector to obtain an expression vector. *E. coli* (BL21) cells were transformed using the vector and induced with isopropylthiogalactopyranoside to obtain a recombinant protein. The recombinant protein was constructed by adding a tag (calmodulin binding protein) N-terminally to the protein of the present invention and the enterokinase recognition site between the tag and the protein of the present invention. The recombinant protein that was affinity purified using a calmodulin affinity column migrated as a single band at about 19 kDa when analyzed using sodium dodecyl sulfate polyacrylamide gel electrophoresis. The N-terminal tag of the purified recombinant protein was cleaved with enterokinase. Free tag protein and enterokinase were removed using affinity columns (calmodulin affinity column and STI-agarose column, respectively) to obtain the protein of the present invention. The recombinant vector was constructed so that the enterokinase-cleaved subject protein had no extra amino acids at its N-terminus and consisted of the amino acid sequence identical to that of the mature protein which is generated in vivo by removal of the N-terminal secretary signal peptide from the precursor protein shown in SEQ ID NO:1 (i.e., 91 amino acids from tyrosine at residue 20 to the C-terminus of SEQ ID NO:1).

Figure 4A:
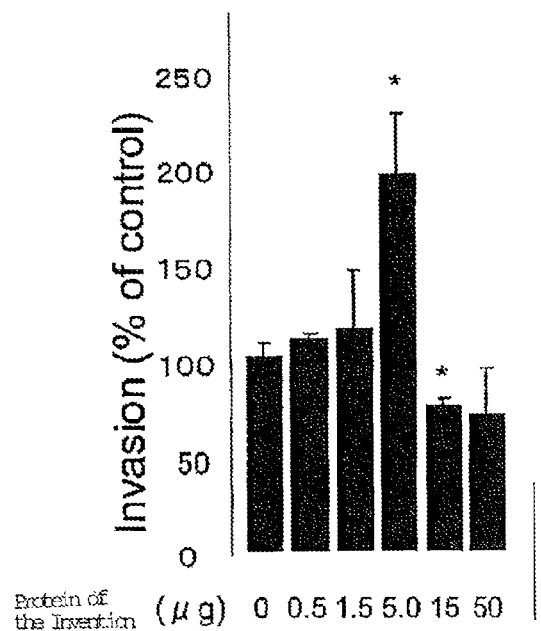
FIG. 4A shows the effect of the recombinant protein of the present invention expressed in *Escherichia coli* on the invasiveness of JAR cells in experiments using Matrigel, an artificial basement membrane matrix.

Assessment of cell invasiveness was carried out using an invasion chamber (BioCoat Matrigel Invasion Chamber, BD Biosciences Corp.) equipped with a filter coated with Matrigel, an artificial basement membrane matrix. JAR cells, a human choriocarcinoma cell line, were obtained from the American Type Tissue Collection. A single cell suspension of JAR cells was prepared at $1 \times 10^5$ cells/mL in serum-free RPMI 1640 by a conventional method. RPMI1640 containing 10% fetal bovine serum (0.75 mL) was added to the lower chamber, while 500 µL of the JAR cell suspension was added to the upper chamber. The invasion chambers were incubated for 18 hours at 37° C. in a humidified 5% $CO_2$ incubator. After incubation, non-invasive cells on the upper surface were removed. JAR cells that had invaded through the Matrigel were stained with Giemsa and observed after the filters were air dried to assess their invasiveness. A bell-shaped dose-response relationship of increasing amount of the recombinant protein of the present invention with JAR cell invasiveness was observed, suggesting that the protein of the present invention regulated the invasiveness of JAR cells (FIG. 4A).

Figure 4B:
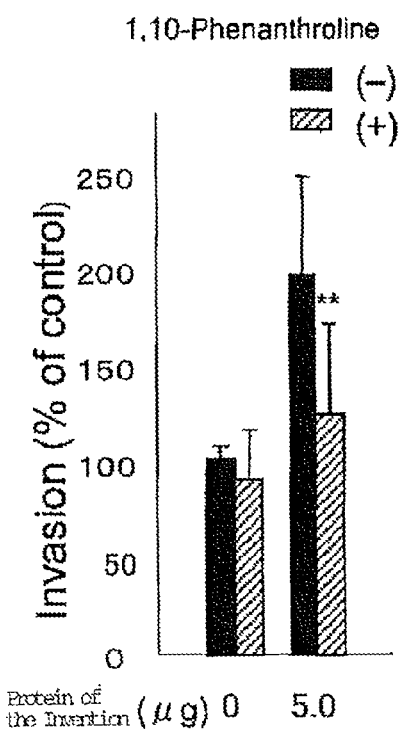
FIG. 4B demonstrates that the promotion activity of the recombinant protein of the present invention expressed in *E. coli* on the invasiveness of JAR cells is inhibited by phenanthroline, a metalloproteinase inhibitor.
Figure 4C:
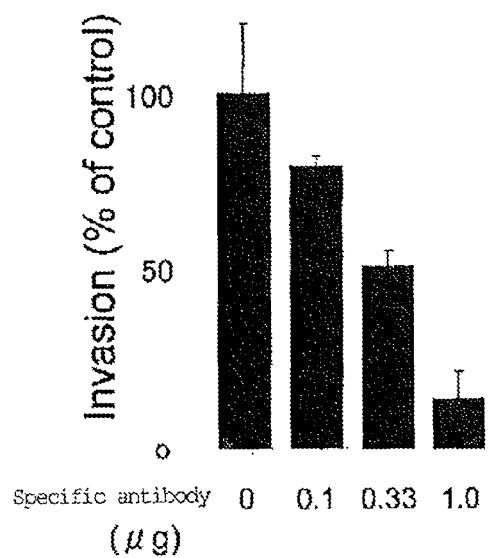
FIG. 4C shows the dose-dependent inhibition of the invasion of JAR cells by a specific antibody against the protein of the present invention.

The metalloproteinase inhibitor phenanthroline inhibited the promotion of JAR cell invasiveness by the recombinant protein of the present invention, suggesting a relationship between the regulatory activity of the subject protein on cell invasiveness and the metalloproteinase activity (FIG. 4B). Furthermore, the effects of the protein of the present invention on cell invasiveness were investigated using the specific antibody used in the immunohistochemical staining, while using rabbit IgG as a control to the antibody. Since the specific antibody against the protein of the present invention inhibited the invasiveness of JAR cells dose-dependently (FIG. 4C), it was confirmed that the protein of the present invention regulates cell invasiveness.

EXAMPLE 5

(Regulation of Smooth Muscle Contraction and Relaxation by the Protein of the Present Invention)

Figure 5A:
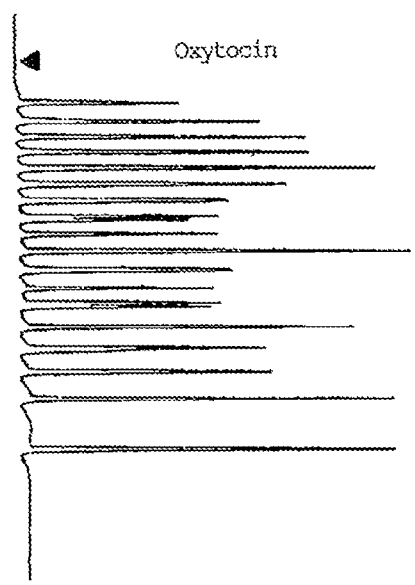
FIG. 5A shows the results obtained by adding oxytocin alone.
Figure 5B:
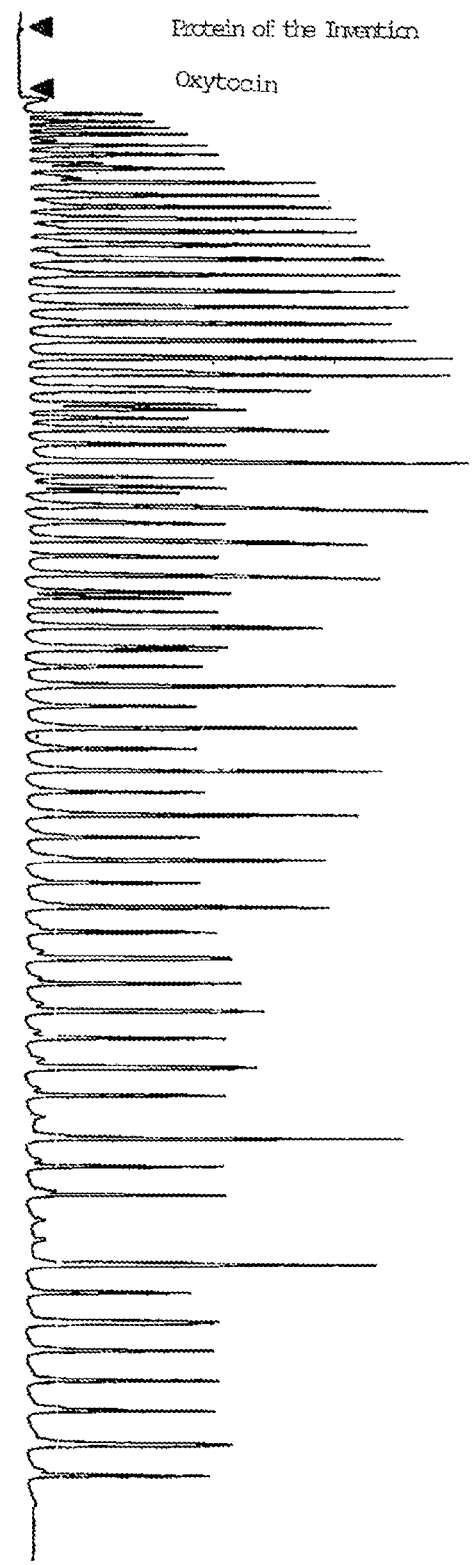
FIG. 5B presents the results obtained by adding the recombinant protein of the present invention 3 minutes prior to oxytocin addition.

The same technique used in the Examples of JP-A No. 2005-210901 was employed. In brief, uteri were removed from timed-pregnant Sprague-Dawley rats on day 21 before the onset of labor and cut into rings approximately 5mm wide. They were mounted in organ chambers filled with Kreb's buffer, maintained at 37° C., and aerated continuously with mixture of 95% $O_2$/5% $CO_2$. Changes in isometric tension were measured. The myometrial contractions obtained by adding 1.07 nM oxytocin after the spontaneous contractions subsided at a basal preload of (0.15 g) are shown in FIG. 5A. After washout, approximately (10 nM) of the recombinant protein of the present invention was applied to the isolated uterine ring of a pregnant rat mounted in a Magnus apparatus 3 minutes before oxytocin addition. As shown in FIG. 5B, pretreatment with the recombinant protein of the present invention resulted in myometrial contractions that persisted for more than 70 minutes with higher frequency and amplitude than those observed when treated with oxytocin alone (FIG. 5A). Therefore, the addition of the protein of the present invention resulted in myometrial contractions that persisted for a longer period of time, which may be analogous to the uterine contractions during labor. Furthermore, after washout of oxytocin and the recombinant protein of the present invention with Kreb's solution, bath application of 1.07 nM oxytocin elicited similar myometrial contractions as shown in FIG. 5A. After another washout with Kreb's solution, similar myometrial contractions as shown in FIG. 5B were observed when approximately (10 nM) of the recombinant protein of the present invention was applied 3 minutes before oxytocin addition. These results indicate that the effect of the recombinant protein on myometrial contraction is reversible upon washout (data not shown). Throughout the entire course of human pregnancy, beginning from fertilization and implantation until the completion of parturition, myometrial contraction and relaxation must be stringently controlled. Considering that the placenta is spatiotemporally in immediate contact with the pregnant uterus, it is suggested that the protein of the present invention might stringently regulate myometrial contraction and relaxation in a paracrine fashion, and is therefore closely involved in the mechanisms of pregnancy maintenance and parturition starting from fertilization and implantation. The inventors of the present invention have already disclosed the inhibitory activity of the protein of the present invention on smooth muscle contraction (i.e., the smooth muscle relaxing activity) in JP-A No. 2005-210901. The present invention has succeeded in disclosing the remarkable characteristics of the protein of the present invention, that is, it possesses stimulatory activity as well as inhibitory activity on myometrial contraction.

The invention claimed is:

1. An isolated antibody which specifically binds to residues 63-70 of SEQ ID NO: 1.

\* \* \* \* \*

UNITED STATES PATENT AND TRADEMARK OFFICE
CERTIFICATE OF CORRECTION

PATENT NO.        : 8,691,954 B2
APPLICATION NO.   : 12/527460
DATED             : April 8, 2014
INVENTOR(S)       : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 110
<212> TYPE: PRT
<213> ORGANISM: Homo sapiens

<400> SEQUENCE: 1

Met Arg Phe Met Thr Leu Leu Phe Leu Thr Ala Leu Ala Gly Ala Leu

```
                1               5              10              15
        Val Cys Ala Tyr Asp Pro Glu Ala Ala Ser Ala Pro Gly Ser Gly Asn
                       20                  25                  30

Pro Cys His Glu Ala Ser Ala Ala Gln Lys Glu Asn Ala Gly Glu Asp
                       35                  40                  45

Pro Gly Leu Ala Arg Gln Ala Pro Lys Pro Arg Lys Gln Arg Ser Ser
                       50                  55                  60

Leu Leu Glu Lys Gly Leu Asp Gly Ala Lys Lys Ala Val Gly Gly Leu
         65                  70                  75                  80

Gly Lys Leu Gly Lys Asp Ala Val Glu Asp Leu Glu Ser Val Gly Lys
                       85                  90                  95

Gly Ala Val His Asp Val Lys Asp Val Leu Asp Ser Val Leu
                      100                 105                 110

<210> SEQ ID NO 2
<211> LENGTH: 605
<212> TYPE: DNA
<213> ORGANISM: Homo sapiens
<220> FEATURE:
<221> NAME/KEY: CDS
<222> LOCATION: (191)..(520)

<400> SEQUENCE: 2
cagccagcct tgttgactt  aacaggtggc tctgaggtgg gagaagagga ggaggagaac     60
acaccactgg aagactggtt cccattggtc cctgtcatgc ttaaaaaaag gcccagagag    120
gcagtcttga caccctagat cccaagatct ccaaggattt ggtggcatac ccactccagc    180
acacagaagc atg agg ttc atg act ctc ctc ttc ctg aca gct ctg gca       229
            Met Arg Phe Met Thr Leu Leu Phe Leu Thr Ala Leu Ala
              1               5                  10 gga gcc ctg gtc tgt gcc tat gat cca gag gcc gcc tct gcc cca gga      277
Gly Ala Leu Val Cys Ala Tyr Asp Pro Glu Ala Ala Ser Ala Pro Gly
         15                  20                  25 tcg ggg aac cct tgc cat gaa gca tca gca gct caa aag gaa aat gca      325
Ser Gly Asn Pro Cys His Glu Ala Ser Ala Ala Gln Lys Glu Asn Ala
 30                  35                  40                  45 ggt gaa gac cca ggg tta gcc aga cag gca cca aag cca agg aag cag      373
Gly Glu Asp Pro Gly Leu Ala Arg Gln Ala Pro Lys Pro Arg Lys Gln
                 50                  55                  60 aga tcc agc ctt ctg gaa aaa ggc cta gac gga gca aaa aaa gct gtg      421
Arg Ser Ser Leu Leu Glu Lys Gly Leu Asp Gly Ala Lys Lys Ala Val
             65                  70                  75 ggg gga ctc gga aaa cta gga aaa gat gca gtc gaa gat cta gaa agc      469
Gly Gly Leu Gly Lys Leu Gly Lys Asp Ala Val Glu Asp Leu Glu Ser
         80                  85                  90 gtg ggt aaa gga gcc gtc cat gac gtt aaa gac gtc ctt gac tca gta      517
Val Gly Lys Gly Ala Val His Asp Val Lys Asp Val Leu Asp Ser Val
 95                 100                 105 cta tagctgtaag gagaagctga gaaatgatac ccaggagcag caggctttac           570
Leu
110 gtcttcagcc taaaacctaa aaaaaaaaaa aaaaa                               605

<210> SEQ ID NO 3
<211> LENGTH: 772
<212> TYPE: DNA
<213> ORGANISM: Homo sapiens
<220> FEATURE:
<221> NAME/KEY: CDS
<222> LOCATION: (191)..(421)
```

<400> SEQUENCE: 3

```
cagccagcct tgttgactt aacaggtggc tctgaggtgg gagaagagga ggaggagaac      60
acaccactgg aagactggtt cccattggtc cctgtcatgc ttaaaaaaag gcccagagag    120
gcagtcttga caccctagat cccaagatct ccaaggattt ggtggcatac ccactccagc    180
acacagaagc atg agg ttc atg act ctc ctc ttc ctg aca gct ctg gca      229
           Met Arg Phe Met Thr Leu Leu Phe Leu Thr Ala Leu Ala
             1               5                  10 gga gcc ctg gtc tgt gcc tat gat cca gag gcc gcc tct gcc cca gga    277
Gly Ala Leu Val Cys Ala Tyr Asp Pro Glu Ala Ala Ser Ala Pro Gly
 15              20                  25 tcg ggg aac cat aaa caa atg gat tgt tta cag cta cag aag ccc cct    325
Ser Gly Asn His Lys Gln Met Asp Cys Leu Gln Leu Gln Lys Pro Pro
 30              35                  40                  45 tca gag act gcc aaa ttt ctg tcc tca tcc acc aac ctg cct aga aga    373
Ser Glu Thr Ala Lys Phe Leu Ser Ser Ser Thr Asn Leu Pro Arg Arg
                 50                  55                  60 gag aag cta gtg ccc tct gca aaa cct ccc cac act agg ggg ctg gta    421
Glu Lys Leu Val Pro Ser Ala Lys Pro Pro His Thr Arg Gly Leu Val
             65                  70                  75 taagggatga aaactagggg gagtctcttt aagcttgcca tgaagcatca gcagctcaaa    481
aggaaaatgc aggtgaagac ccagggttag ccagacaggc accaaagcca aggaagcaga    541
gatccagcct tctggaaaaa ggcctagacg gagcaaaaaa agctgtgggg ggactcggaa    601
aactaggaaa agatgcagtc gaagatctag aaagcgtggg taaggagcc gtccatgacg    661 ttaaagacgt ccttgactca gtactatagc tgtaaggaga agctgagaaa tgatacccag    721
gagcagcagg ctttacgtct tcagcctaaa acctaaaaaa aaaaaaaaaa a            772

<210> SEQ ID NO 4
<211> LENGTH: 670
<212> TYPE: DNA
<213> ORGANISM: Homo sapiens
<220> FEATURE:
<221> NAME/KEY: CDS
<222> LOCATION: (191)..(553)

<400> SEQUENCE: 4
cagccagcct tgttgactt aacaggtggc tctgaggtgg gagaagagga ggaggagaac      60
acaccactgg aagactggtt cccattggtc cctgtcatgc ttaaaaaaag gcccagagag    120
gcagtcttga caccctagat cccaagatct ccaaggattt ggtggcatac ccactccagc    180
acacagaagc atg agg ttc atg act ctc ctc ttc ctg aca gct ctg gca      229
           Met Arg Phe Met Thr Leu Leu Phe Leu Thr Ala Leu Ala
             1               5                  10 gga gcc ctg gtc tgt gcc tat gat cca gag gcc gcc tct gcc cca gga    277
Gly Ala Leu Val Cys Ala Tyr Asp Pro Glu Ala Ala Ser Ala Pro Gly
 15              20                  25 tcg ggg aac cct tgc cat gaa gca tca gca gct caa aag gaa aat gca    325
Ser Gly Asn Pro Cys His Glu Ala Ser Ala Ala Gln Lys Glu Asn Ala
 30              35                  40                  45 ggt gaa gac cca ggg tta gcc aga cag gca cca aag cca agg aag cag    373
Gly Glu Asp Pro Gly Leu Ala Arg Gln Ala Pro Lys Pro Arg Lys Gln
                 50                  55                  60 aga tcc agc ctt ctg gaa aaa ggc cta gac gga gca aaa aag ctg tg     421
Arg Ser Ser Leu Leu Glu Lys Gly Leu Asp Gly Ala Lys Lys Ala Val
             65                  70                  75 ggg gga ctc gga aaa cta gga aaa gat gca gtc gaa gat cta gaa agc    469
Gly Gly Leu Gly Lys Leu Gly Lys Asp Ala Val Glu Asp Leu Glu Ser
         80                  85                  90
```

-continued

```
gtg ggt aaa ggt ggg gaa gag agg ttg gtc ttt ggg gct cct gtg aat      517
Val Gly Lys Gly Gly Glu Glu Arg Leu Val Phe Gly Ala Pro Val Asn
    95                  100                 105 cta acc tcc atc cct ctg act tct gtg agc cgt cca tgacgttaaa gacgtc    569
Leu Thr Ser Ile Pro Leu Thr Ser Val Ser Arg Pro
110                 115                 120 cttgactcag tactatagct gtaaggagaa gctgagaaat gatacccagg agcagcaggc    629
tttacgtctt cagcctaaaa cctaaaaaaa aaaaaaaaa a                         670

<210> SEQ ID NO 5
<211> LENGTH: 22
<212> TYPE: PRT
<213> ORGANISM: Homo sapiens

<400> SEQUENCE: 5

Tyr Asp Pro Glu Ala Ala Ser Ala Pro Gly Ser Gly Asn Pro Cys His
1               5                   10                  15

Glu Ala Ser Ala Ala Gln
            20

<210> SEQ ID NO 6
<211> LENGTH: 29
<212> TYPE: PRT
<213> ORGANISM: Homo sapiens

<400> SEQUENCE: 6

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu
            20                  25
```